(12) United States Patent
Lary et al.

(10) Patent No.: US 7,232,687 B2
(45) Date of Patent: Jun. 19, 2007

(54) MULTIPLE SORTER MONITOR AND CONTROL SUBSYSTEM FOR FLOW CYTOMETER

(75) Inventors: Todd P. Lary, Homestead, FL (US); Robert C. Burr, Miami, FL (US); Christopher W. Snow, Homestead, FL (US)

(73) Assignee: Beckman Coulter, Inc., Fullerton, CA (US)

(*) Notice: Subject to any disclaimer, the term of this patent is extended or adjusted under 35 U.S.C. 154(b) by 385 days.

(21) Appl. No.: 10/819,745

(22) Filed: Apr. 7, 2004

(65) Prior Publication Data

US 2005/0227362 A1    Oct. 13, 2005

(51) Int. Cl.
  G01N 33/48   (2006.01)
  G01N 21/64   (2006.01)
  B07C 5/342   (2006.01)

(52) U.S. Cl. .......................... 436/63; 209/3.1; 209/3.2; 209/3.3; 209/4; 209/127.4; 209/552; 209/571; 209/576; 209/577; 209/578; 209/579; 209/906; 250/461.2; 422/73; 422/82.05; 422/82.08; 422/82.09; 422/82.11; 436/164; 436/172

(58) Field of Classification Search ................. 209/3.1, 209/3.2, 3.3, 4, 127.4, 552, 571, 576–579, 209/906; 250/461.2; 422/73, 82.05, 82.08–82.09, 422/82.11; 436/63, 164, 172
See application file for complete search history.

(56) References Cited

U.S. PATENT DOCUMENTS

| | | | | |
|---|---|---|---|---|
| 3,826,364 A | * | 7/1974 | Bonner et al. ............... | 209/3.1 |
| 4,097,373 A | * | 6/1978 | Allred ......................... | 209/130 |
| 4,564,598 A | * | 1/1986 | Briggs ......................... | 436/501 |
| 4,667,830 A | * | 5/1987 | Nozaki et al. ............... | 209/3.1 |
| 4,676,640 A | * | 6/1987 | Briggs ......................... | 356/317 |
| 4,702,598 A | * | 10/1987 | Bohmer ....................... | 356/343 |
| 4,934,811 A | * | 6/1990 | Watts et al. .................. | 356/73 |
| 4,987,539 A | * | 1/1991 | Moore et al. ................. | 356/39 |
| 6,079,836 A | * | 6/2000 | Burr et al. .................... | 356/70 |
| 6,372,506 B1 | * | 4/2002 | Norton ......................... | 436/63 |

* cited by examiner

Primary Examiner—Arlen Soderquist
(74) Attorney, Agent, or Firm—Charles E. Wands; Mitchell E. Alter

(57) ABSTRACT

An optical illumination and monitoring subsystem controls the operation of a flow cytometer having a carrier fluid that flows along a channel coupled to a droplet generator, which controls a point at which droplets break off from the carrier fluid, and a droplet sorter that is operative to cause selected droplets to be sorted along one or more droplet travel paths. The subsystem is operative to illuminate a respective droplet monitoring location along each of one or more droplet travel paths with a respective beam of light, such as that sourced from a common laser. In response to backscatter reflection from a droplet passing through the respective beam of light at a respective droplet monitoring location, the amplitude of the beam of light is increased. Then the droplet is monitored for the presence of a particle therein exhibiting detectable fluorescence as a result of the increase in the amplitude of the respective beam of light.

11 Claims, 5 Drawing Sheets

US 7,232,687 B2

MULTIPLE SORTER MONITOR AND CONTROL SUBSYSTEM FOR FLOW CYTOMETER

FIELD OF THE INVENTION

The present invention relates in general to flow cytometer systems and subsystems therefor, and is particularly directed to a new and improved subsystem that is operative to setup and monitor multiple sorting paths for non-deflected and deflected droplet streams, in order to provide for downstream-based adjustment of drop-formation and drop-sorting deflection parameters of the flow cytometer.

BACKGROUND OF THE INVENTION

As described in the U.S. Patent to Burr et al, U.S. Pat. No. 6,079,836 (hereinafter referred to as the '836 patent), entitled: "Flow Cytometer Droplet Break-Off Location Adjustment Mechanism," assigned to the assignee of the present application and the disclosure of which is incorporated herein, flow cytometers, such as that shown diagrammatically in FIG. 1, are commonly employed in the medical industry to analyze particles in a patient's body fluid (e.g., blood cells) as an adjunct to the diagnosis and treatment of disease. As a non-limiting example, in the course of chemotherapy treatment, such instruments may be used to sort and collect healthy blood cells (stem cells) from a quantity of blood that has been removed from the patient's bone marrow prior to chemotherapy. Once a chemotherapy treatment session has been completed, a collected quantity of these cells is then reinjected back into the patient, to facilitate migration and healthy blood cell regeneration.

For this purpose, in the flow cytometer system shown in FIG. 1, particles to be analyzed, such as cells of a centrifuged blood sample stored in a container 11, are injected into a (pressurized) continuous or uninterrupted stream of carrier fluid (e.g., saline) 12. The carrier fluid stream is directed along a flow channel 13 of a fluid flow chamber 14. The fluid flow channel 13 is intersected at an 'upstream' location 15 by an output light beam 16 emitted by an optical illumination subsystem, such as a one or more lasers 17. Located optically in the path of the laser output beam 16 after its being intercepted by the carrier fluid stream are one or more photodetectors of a photodetector subsystem 20. The photodetector subsystem is positioned to receive light that has been modulated by the contents of (particles/cells within) the fluid stream, including light reflected off a cell, the blocking of light by a cell, and a light emission from a fluorescent dye antibody attached to a cell.

In order to avoid confusion as to which photodetector output signal is representative of which illuminated cell, the fluid flow chamber 13 through the cytometer flow chamber is configured and sized to pass the particles or cells only one cell at the time through the intersection location 15 with the laser's output beam 16. As a consequence, as output signals from the photodetector subsystem 20 are modulated by particles transported by the carrier fluid stream, each modulation signal can be associated with an individual cell. If the output of the photodetector subsystem 20 satisfies prescribed 'sort' criteria associated with one or more parameters of a desired cell, it is used to control the sorting of a droplet 23 of carrier fluid containing that cell by an electrostatic droplet sorter located 'downstream' of an exit port 18 of the fluid flow chamber.

The carrier fluid stream is converted into individual droplets by an acoustically (e.g., piezoelectric transducer) driven droplet generator 27, which is coupled to the fluid flow chamber. The fluid stream leaving the exit port 18 proceed as an interconnected droplet stream 22 and then break off into separate droplets at a location 25 downstream of the chamber exit port. Also there is a 'sort' delay between the time that a cell passes through the laser intersection location 15 and a subsequent time at which the last attached portion of the carrier fluid stream containing that particular cell actually physically separates or breaks off from the carrier fluid stream as a distinct droplet 23 traveling along a travel path 26.

The location 25 at which the droplets form downstream of the flow chamber exit port 18 may be adjusted by varying parameters of the droplet generator drive signal. The rate at which droplets are formed is governed by the frequency of the acoustic drive signal, and the droplets become synchronized with the frequency of the piezo vibration of the droplet generator 27. As a non-limiting example, the acoustic drive frequency applied to the droplet generator 27 may be on the order of from four to one hundred KHz, at a fluid pressure on the order of from three to seventy psi.

The photodetector output is typically digitized and then analyzed by a cell type mapping or identification algorithm executed by an associated supervisory control processor of the flow cytometer's control workstation 50. Based upon this analysis, the control processor supplies control signals to a charging and deflection control circuit 52 of the droplet sorter 24 to sort or abort the droplet. In order to controllably sort an individual droplet 23 that breaks off or separates from the fluid stream exiting the flow chamber's exit port 18, the droplet sorter employs an electrostatic charging collar 31, which surrounds the travel path 26 of the droplet sequence. The charging collar may comprise a metallic cylinder that is located so as to surround the location along the droplet sequence travel path 26 where the individual droplets 23 separate from the fluid stream, and is typically several droplets in (axial) length. The charging collar 31 is positioned vertically downstream of the fluid chamber exit port 18 and upstream of an associated set of electrostatic (opposite polarity, high voltage) deflection plates 33 and 35 between which the stream of charged droplets 23c pass as they travel downwardly and are either sorted along one or more sorting paths 36 into associated sorted droplet collection containers 41, or are allowed to pass unsorted along travel path into an aborted or discarded wasted container 43. The center position is not always a waste container—as it may alternatively be employed as a collection container for collecting the sample that went through the instrument, not to waste it.

Under the control of the cell analysis and sorting routine executed by the cytometer workstation 50, a prescribed charging voltage pulse of a given duration is selectively applied to the charging collar, so as to charge a droplet that should contain the cell to be sorted. As the selectively charged droplet passes between the two opposite polarity high voltage deflection plates 33 and 35, it is attracted to the plate with the opposite charge, while being simultaneously repelled by the plate with the same or like charge. This electrostatic steering action directs the charged droplet along a deflected travel path that is off axis to the unsorted droplet travel path and into a sorted droplet collection container 41.

As noted above, for any given cell or particle of interest within the fluid stream, there is a 'sort' delay between the time at which the photodetector subsystem 20 generates an output signal for a particular cell, and the time of the sorting pulse at which a droplet 23 containing the cell actually individually separates or breaks of from the fluid stream.

Knowing the exact duration of this sort delay is critical to accurate sorting of the droplets, since only the last attached droplet that breaks off from the fluid stream at the time of the applied sort charging pulse will be deflected by the deflection plates and subsequently collected into the sorted droplet collection container.

In accordance with the invention described in the '836 patent the flow cytometer is provided with a feedback-based signal processing mechanism that is operative to maintain the droplet break-off point at an initially calibrated spatial location (within the droplet charged collar of the droplet sorting mechanism) by means of a downstream optical detector subsystem, that looks for gaps in the fluid droplet stream that have been created by the deflection of charged droplets. The difference between the times at which these gaps are detected at a prescribed downstream location in the path of the droplet stream and the times at which deflected droplets that created the gaps were charged at the droplet charge collar is compared with a calibration reference interval. Any difference between the two is employed to adjust the amplitude of the piezo drive to the droplet generator, as necessary, to bring the instrument back into calibration. It has also been determined that controlling the temperature of the fluid stream and the pressure of the fluid stream can be as or more effective in correcting any differences.

SUMMARY OF THE INVENTION

The present invention is similar to the subsystem described in the '836 patent in that it is directed to an auxiliary optical subsystem that is installed at the break-off point and at positions downstream of the droplet break-off point, and which is used to monitor the composition of the sorted droplet stream. However, in addition to looking for gaps in the stream as in the '836 patent, the present invention places auxiliary illumination and detection units adjacent to monitoring locations in each droplet travel path. The illumination and monitoring stations are positioned relatively close to the droplet break-off point, so as to minimize the effects of drag on the droplets. The purpose of each illumination and monitoring station is to detect droplets as they pass through a viewing zone of the station and, once a droplet is detected, to illuminate that droplet with a pulse of high energy laser light that will cause a particle that may be contained within the droplet to fluoresce at an amplitude that can be readily detected.

For this purpose, each illumination and monitoring station contains an illumination and reception lens unit whose field of view is sized to encompass a respective droplet traveling along the path adjacent to which the lens has been placed. Coupled to a respective lens is an optical fiber termination block that terminates a set of three groups of optical fibers. A first of these optical fibers is coupled to the output of a continuous output and controllably pulsed shared optical illumination source, such as a diode laser. It is through this first fiber, in cooperation with the laser, that a droplet intersection point along the travel path, adjacent to which the termination block and associated lens has been placed, is continuously and controllably illuminated. A respective optical fiber termination block is positioned so that light from its associated laser insects the droplet travel path transversely.

A second optical fiber is coupled to a diode sensor which is operative to detect light that is scattered off a droplet as the droplet passes through a respective one of the illumination and monitoring stations. A third optical fiber is coupled to another diode sensor which contains an integrated long pass filter to exclude laser backscatter from the droplet. This diode sensor is used to detect fluorescence generated by a particle that may be present in the droplet passing by its associated illumination and monitoring station.

The amplitude of a fluorescent pulse that is normally produced by a particle within an illuminated droplet is relatively low, especially when compared to the amplitude of a backscattered light pulse off the droplet. In accordance with the invention, this potential low amplitude detection problem is readily overcome by controllably increasing the amplitude of the illumination beam produced by the laser, in response to detecting that a backscattered light pulse has reached a predetermined threshold. When this occurs, the energy in the illumination laser beam is briefly increased or pulsed so as to stimulate a fluorescent particle within the droplet (if present) to fluoresce at a substantially increased amplitude. The amplitude of the substantially increased fluorescence emitted by the particle in the droplet and is readily detectable by the fluorescence diode sensor. The fluorescence will not be greater than the scatter.

A particularly beneficial aspect of the present invention is its ability to confirm that the droplets have been sorted into their intended paths. Namely, being located downstream of the droplet break-off point enables the diode detector outputs to not only indicate which droplets contain particles, but whether the fluorescent characteristics of those particles are properly associated with their intended travel paths. This information is fed back to the cytometer's cell analysis and sorting routine executed by the cytometer workstation, which then makes whatever adjustments are appropriate to ensure proper sorting of the droplets along their intended deflection paths.

DETAILED DESCRIPTION

Figure 1:
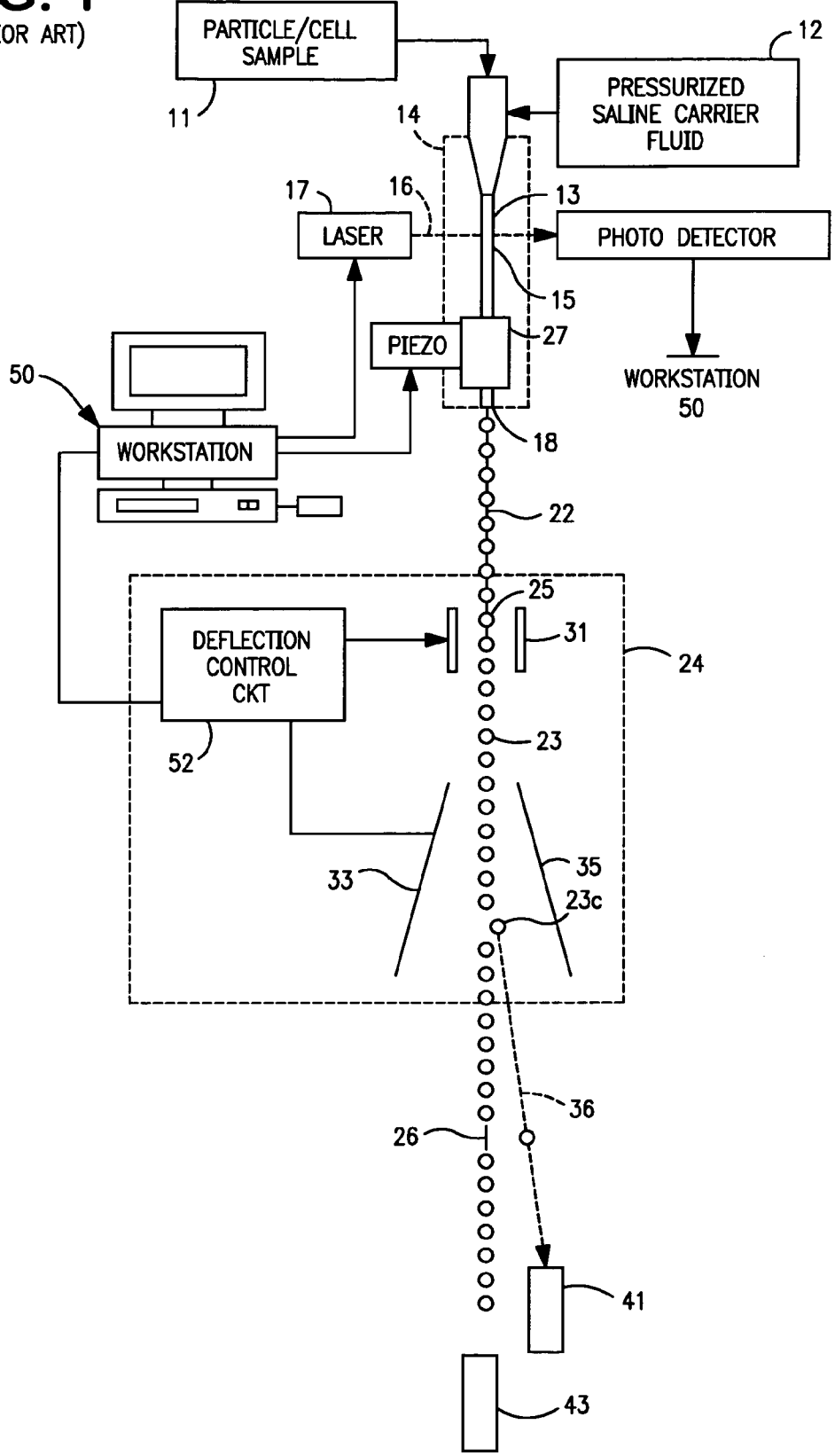
FIG. 1 diagrammatically illustrates the general instrumentation architecture of a flow cytometer.

Before describing in detail the new and improved multi-path installed droplet monitoring subsystem in accordance with the present invention, it should be observed that the invention resides primarily in what is effectively a prescribed arrangement of conventional flow cytometer instrumentation and associated signal processing components and attendant supervisory control circuitry therefor, that controls the operations of such circuits and components. Consequently, the configuration of such circuits and components and the manner in which they are interfaced with other cytometer system equipment have, for the most part, been illustrated in the drawings in readily understandable block diagram format, which show only those specific details that are pertinent to the invention, so as not to obscure the disclosure with details which will be readily apparent to those skilled in the art having the benefit of the description herein. Thus, the block diagram illustrations are intended to show the major components of a flow cytometer system in a convenient functional grouping, whereby the present invention may be more readily understood.

Figure 2:
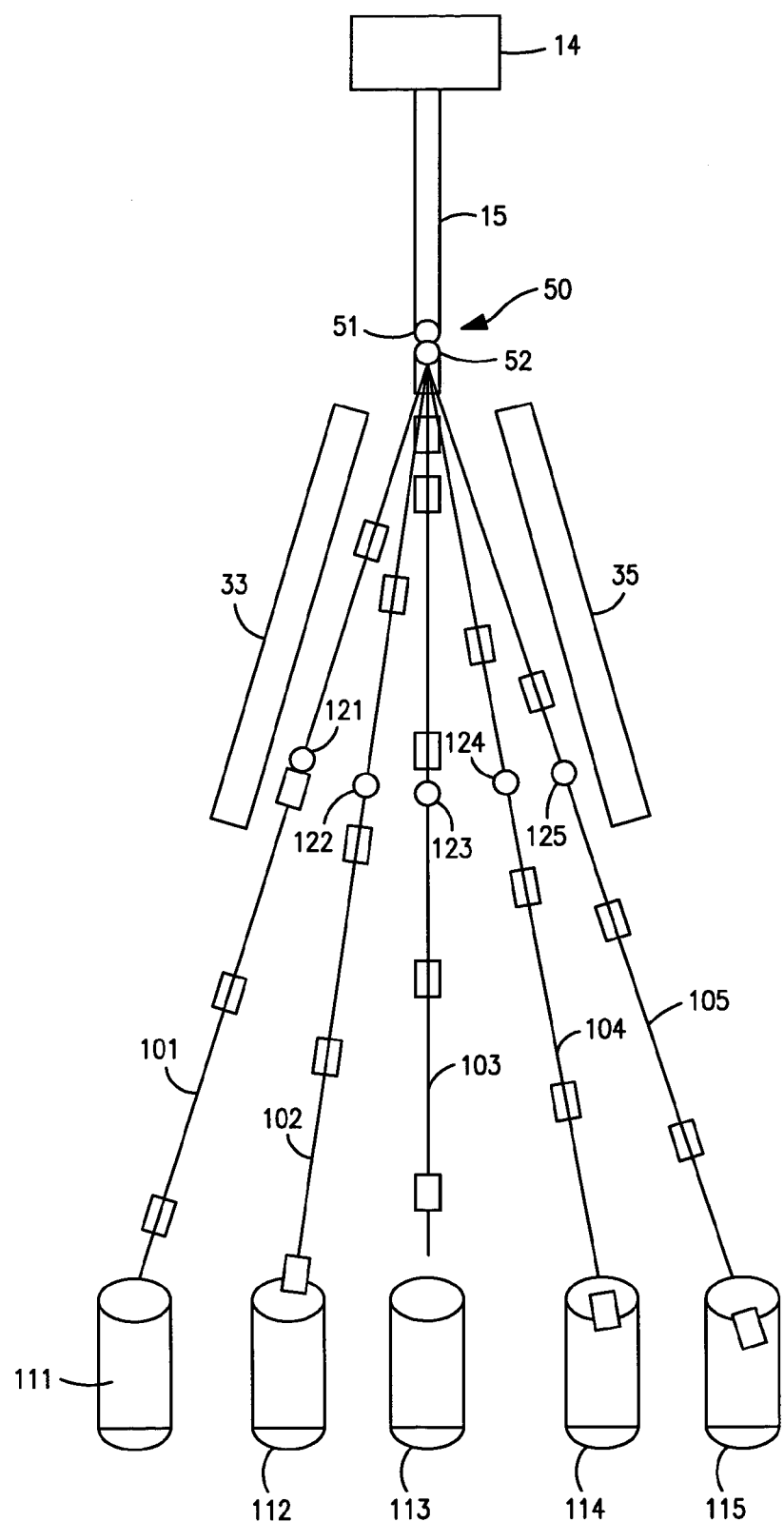
FIG. 2 diagrammatically illustrates the auxiliary multi-path droplet monitoring subsystem of the invention, and the manner in which it is interfaced with a flow cytometer system of the type illustrated in FIG. 1.

Attention is now directed to FIG. 2 which diagrammatically illustrates the auxiliary multi-path droplet monitoring subsystem of the invention, and the manner in which it is interfaced with a flow cytometer system of the type illustrated in FIG. 1, described above. In the illustration in FIG. 2 and subsequent diagrams, the continuous fluid stream is diagrammatically depicted as is a relatively long rectangle, while individual droplets that have broken off from the continuous fluid stream at the exit port of the fluid chamber are shown as relatively small rectangles. Image observation points, at which optical illumination and detector components are located are denoted as circles.

Figure 4:
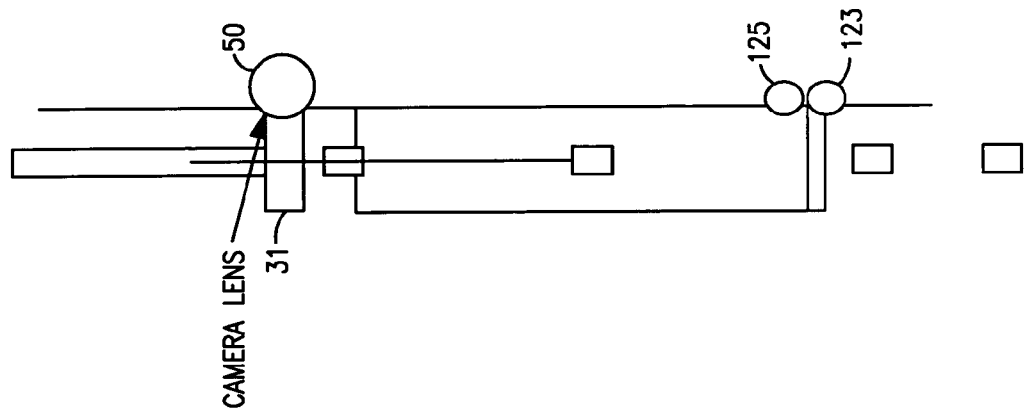
FIGS. 3 and 4 are respective front and side views of the droplet break-off optical detection subsystem of the invention.

As shown therein, a droplet break-off optical detection subsystem 50, which may comprise a pair of break-off optical sensors 51 and 52, such as photodiodes or a camera, is disposed immediately adjacent to the droplet break off point. As further shown in the front view of FIG. 3 and the side view of FIG. 4, the droplet break-off optical detection subsystem may be located coaxially with the charging collar 31. In addition to the optical break-off detection subsystem, the present invention contains a plurality of illumination and optical monitoring stations that are respectively positioned adjacent to prescribed positions along each of the travel paths through which one or more droplets may pass depending upon the degree, if any, of charging of a droplet as it exits the charging plates and is deflected by the opposite polarity voltages applied to the droplet deflection plates 33 and 35.

Figure 3:
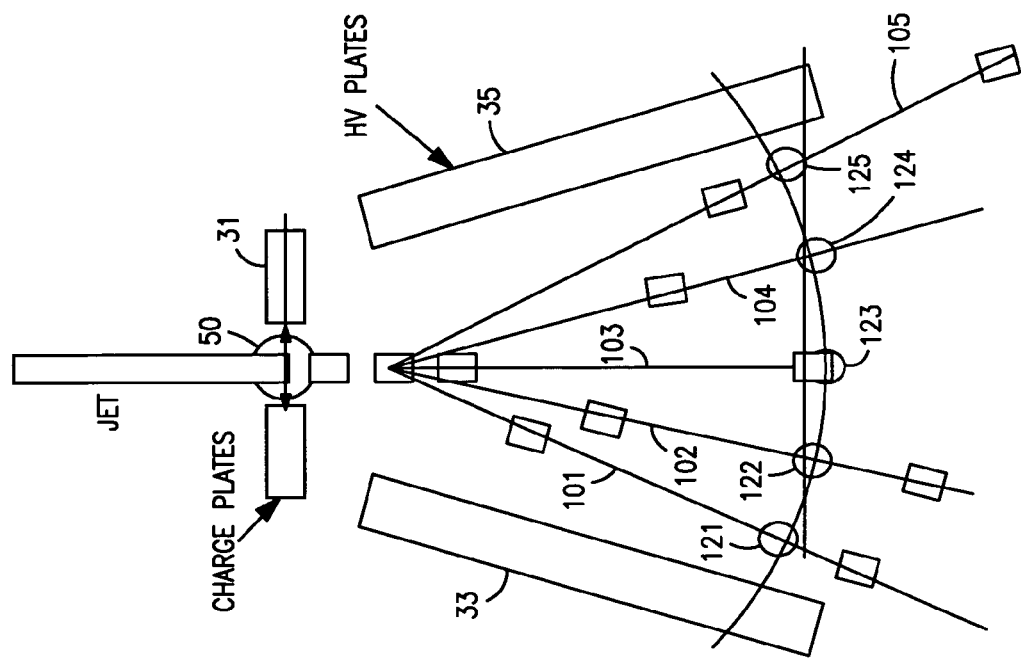

For purposes of providing a non-limiting example, FIGS. 2 and 3 show a cytometer subsystem containing five travel paths 101, 102, 103, 104 and 105, that respectively terminate at droplet collection receptacles 111, 112, 113, 114 and 115. Of these five, the central-most path 103 is associated with unsorted or aborted droplets, while paths 101 and 102 sort to the left of the central axis of the sorter, and paths 104 and 105 sort to the right of the central axis of the sorter. As noted above, a path illumination and monitoring station is positioned immediately adjacent to each path. For the five path embodiment of the present example, there are five illumination and monitoring stations denoted by circles 121, 122, 123, 124 and 125, respectively associated with travel paths 101, 102, 103, 104 and 105. Pursuant to a preferred embodiment of the invention, the illumination and monitoring stations are positioned relatively close to the droplet break-off point, so as to minimize the effects of drag on the droplets. As can be seen from the diagrammatic illustrations of FIGS. 2 and 3, the illumination and monitoring stations may be placed along an arc that is bounded by the high voltage electrostatic deflection plates.

Figure 5:
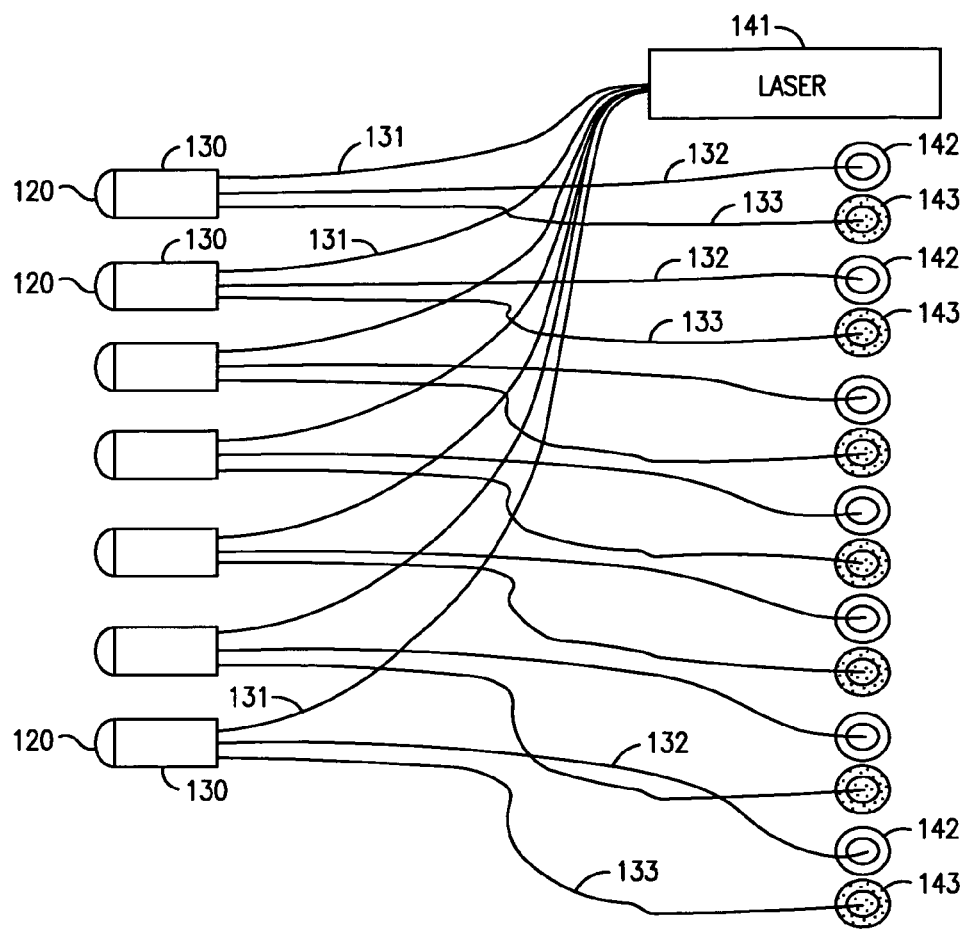
FIG. 5 shows the coupling of a plurality optical fiber termination and lens units to a laser and sets of diode detectors.
Figure 6:
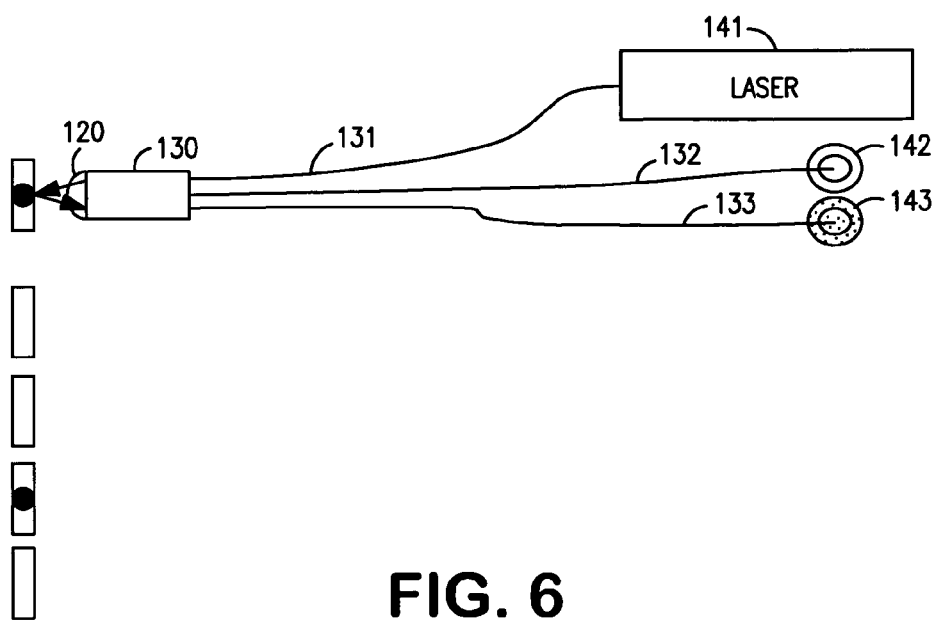
FIG. 6 shows the coupling of an individual optical fiber termination and lens unit to a laser and a set of diode detectors.

Each circle represents an illumination and reception lens unit having a viewing zone that is sized to encompass a respective droplet traveling along the path adjacent to which the lens has been placed. As further shown in FIG. 5, and also in FIG. 6, coupled to a respective lens 120 is an optical fiber termination block 130 that terminates a set of three optical fibers 131, 132 and 133. A first of these optical fibers, fiber 131, is coupled to the output of an associated optical illumination source, such as a diode laser 141. It is through this first fiber 131, in cooperation with laser 141, that a droplet intersection point along the travel path, adjacent to which the termination block and associated lens has been placed, is continuously and controllably illuminated. A respective optical fiber termination block is positioned so that light from its associated laser insects the droplet travel path transversely.

A second optical fiber 132 is coupled to a diode sensor 142, which is operative to detect light that is scattered off a droplet as the droplet passes through a respective one of the illumination and monitoring stations 121, 122, 123, 124 and 125. A third optical fiber 133 is coupled to another diode sensor 143, which contains an integrated long pass filter to exclude laser backscatter from the droplet. This diode sensor 143 is used to detect fluorescence generated by a particle that may be present in the droplet passing by the illumination and monitoring station.

Figure 7:
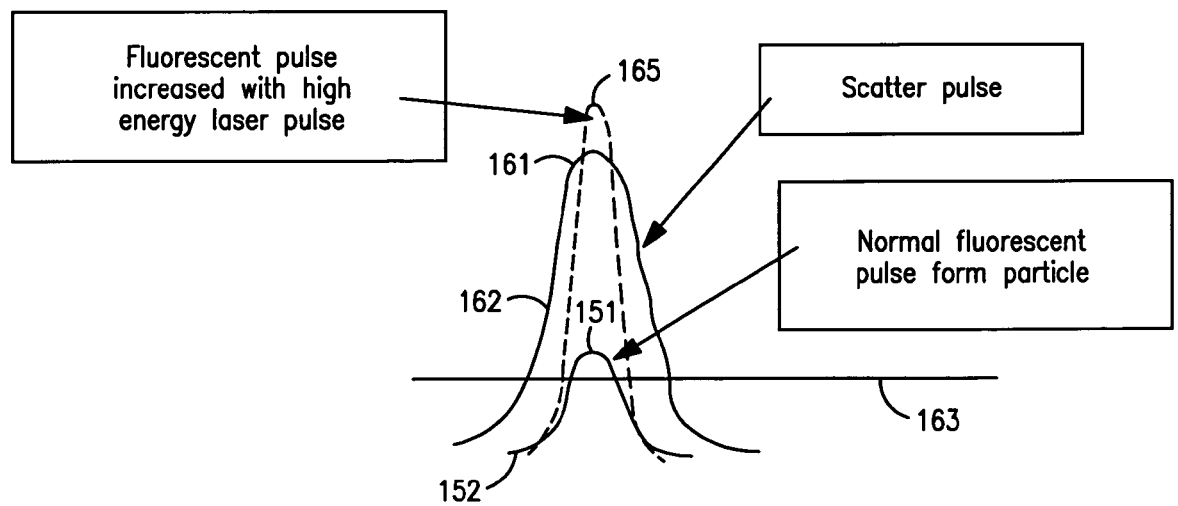
FIG. 7 shows outputs produced by a respective pair of backscatter and fluorescence diode detectors.

As shown in FIG. 7, the amplitude 151 of a fluorescent pulse 152 that is normally produced by a particle within an illuminated droplet is relatively low, especially when compared to the amplitude 161 of a backscattered light pulse 162 off the droplet. In accordance with the invention, this potential low amplitude problem is readily overcome by controllably increasing the amplitude of the illumination beam produced by the laser 141, in response to detecting that backscattered light pulse 162 has reached a predetermined threshold 163. When this occurs, the energy in the illumination laser beam is briefly increased or pulsed so as to stimulate a fluorescent particle within the droplet (if present) to fluoresce at a substantially increased amplitude, as shown by dotted lines 165 in FIG. 7. The amplitude of the substantially increased fluorescence emitted by the particle in the droplet is now readily detectable by the diode sensor 143, especially in the context of diode sensor 143 being provided with an integrated long pass filter to exclude the laser scatter.

It may be noted that backscattering of the laser light beam off a passing droplet is initially detected as the forwardmost end of the droplet enters the illumination field of view of the lens 120. This serves to immediately trigger the pulsing of the laser diode with an increased energy output, so that the location of a fluorescing particle within the droplet may be readily identified.

A particularly beneficial aspect of the present invention is its ability to confirm that the droplets have been sorted into their intended paths. Namely, being located downstream of the droplet break-off point enables the diode detector outputs to not only indicate which droplets contain particles, but whether the fluorescent characteristics of those particles are properly associated with their intended travel paths. This information is fed back to the cytometer's cell analysis and sorting routine executed by the cytometer workstation 50, which then makes whatever adjustments are appropriate to ensure proper sorting of the droplets along their intended deflection paths.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein, but intend to cover all such changes and modifications as are obvious to one of ordinary skill in the art.

What is claimed:

1. A method of controlling the operation of a flow cytometer, wherein a carrier fluid flows along a channel coupled to a droplet generator that controls a point at which droplets break off from said carrier fluid, and a droplet sorter is operative to cause selected droplets to be sorted along one or more droplet travel paths, said method comprising the steps of:

(a) illuminating a respective droplet monitoring location along each of said one or more droplet travel paths with a respective beam of light;

(b) in response to backscatter reflection from a droplet passing through said respective beam of light at said respective droplet monitoring location, causing an increase in the amplitude of said respective beam of light; and (c) monitoring said droplet for the presence of a particle therein exhibiting detectable fluorescence as a result of said increase in the amplitude of said respective beam of light.

2. The method according to claim 1, further comprising the step of (d) controlling at least one of said droplet generator and said droplet sorter in accordance with the extent to which step (c) detects fluorescence from said droplet.

3. The method according to claim 1, wherein step (a) comprises illuminating said respective droplet monitoring location with a laser beam that is directed upon said respective droplet monitoring location by means of an optical fiber and an associated focusing lens.

4. The method according to claim 3, wherein step (b) comprises directing said backscatter reflection through an optical fiber for delivery to an optical detector for said backscatter reflection.

5. The method according to claim 4, wherein step (c) comprises directing said fluorescence through an optical fiber for delivery to an associated optical fluorescence detector.

6. The method according to claim 5, wherein said optical fluorescence detector includes an integrated long pass filter that is operative to exclude the passage therethrough of backscatter light.

7. An arrangement for controlling the operation of a flow cytometer, wherein a carrier fluid flows along a channel coupled to a droplet generator that controls a point at which droplets break off from said carrier fluid, and a droplet sorter is operative to cause droplets to be sorted along a plurality of droplet travel paths, said arrangement comprising:

a plurality of droplet monitoring locations respectively disposed adjacent to said droplet travel paths;

a plurality of laser outputs coupled to respective droplet monitoring locations by means of optical fibers and focusing lenses associated therewith;

a plurality of backscatter detectors respectively coupled by means of optical fibers to said droplet monitoring locations; and a plurality of fluorescence detectors respectively coupled by means of optical fibers to said droplet monitoring locations, and wherein a respective one of said lasers is operative to increase energy in the laser beam emitted thereby in response to an associated backscatter detector detecting backscatter reflection from a droplet passing through a respective beam of light at a respective droplet monitoring location.

8. The arrangement according to claim 7, wherein the operation of at least one of said droplet generator and said droplet sorter is controlled in accordance with the extent to which a fluorescence detector detects fluorescence from a droplet.

9. The arrangement according to claim 7, wherein a respective optical fluorescence detector includes an integrated long pass filter that is operative to exclude the passage therethrough of backscatter light.

10. An optical illumination and monitoring apparatus for controlling the operation of a flow cytometer, said flow cytometer having a carrier fluid which flows along a channel coupled to a droplet generator that controls a point at which droplets break off from said carrier fluid, and a droplet sorter that is operative to cause droplets to be sorted along a plurality of droplet travel paths, said apparatus comprising:

a plurality of droplet monitoring locations respectively disposed adjacent to said droplet travel paths;

a plurality of laser outputs coupled to respective droplet monitoring locations by means of optical fibers and focusing lenses associated therewith;

a plurality of backscatter detectors respectively coupled by means of optical fibers to said droplet monitoring locations, and wherein a respective laser is operative to increase energy in the laser beam emitted thereby in response to an associated backscatter detector detecting backscatter reflection from a droplet passing through a respective beam of light at a respective droplet monitoring location; and a plurality of fluorescence detectors respectively coupled by means of optical fibers to said droplet monitoring locations, a respective fluorescence detector being operative to detect an increased amplitude fluorescence pulse resulting from said increase in energy in the laser beam emitted by an associated one of said lasers; and wherein the operation of at least one of said droplet generator and said droplet sorter is controlled in accordance with the extent to which a fluorescence detector detects increased amplitude fluorescence from a droplet.

11. The apparatus according to claim 10, wherein a respective optical fluorescence detector includes an integrated long pass filter that is operative to exclude the passage therethrough of backscatter light.

* * * * *